(12) United States Patent
Yeh

(10) Patent No.: US 6,619,104 B1
(45) Date of Patent: Sep. 16, 2003

(54) CONTINUOUS TESTING DEVICE FOR WATER PIPE

(75) Inventor: Ching Zeng Yeh, Kaohsiung (TW)

(73) Assignee: Kuo Toon International Co., Ltd., Kaoshiung (TW)

( * ) Notice: Subject to any disclaimer, the term of this patent is extended or adjusted under 35 U.S.C. 154(b) by 0 days.

(21) Appl. No.: 10/170,930

(22) Filed: Jun. 12, 2002

(51) Int. Cl.[7] ................................................ G01M 3/04
(52) U.S. Cl. ............................ 73/49.6; 73/49.5; 73/49.1
(58) Field of Search ........................... 73/807, 862.581, 73/862.584, 862.582, 862.583, 49.5, 49.6, 49.1

(56) References Cited

U.S. PATENT DOCUMENTS

| | | | | |
|---|---|---|---|---|
| 4,182,160 A | * | 1/1980 | Powers et al. | 73/49.5 |
| 4,211,107 A | * | 7/1980 | Sleeter et al. | 73/49.6 |
| 4,416,147 A | * | 11/1983 | Hasha | 73/49.6 |
| 4,586,379 A | * | 5/1986 | Burkhardt, Jr. | 73/622 |
| 4,858,464 A | * | 8/1989 | Miller et al. | 73/49.5 |

* cited by examiner

Primary Examiner—Edward Lefkowitz
Assistant Examiner—Andre Allen
(74) Attorney, Agent, or Firm—Pro-Techtor International Services

(57) ABSTRACT

A continuous testing device for a water pipe, comprising a frame, a left fixed plate and a right fixed plate, a tested pipe section, a compensating pipe section, a central plate, two horizontal oil pressure cylinders, a vertical oil pressure cylinder, and a connecting tube. The left and right fixed plates provide fixed bases at left and right ends of the frame. The tested and compensating pipe sections are located between the left and right fixed plates. The tested pipe section is a tube body that allows monitoring. The compensating pipe section, separated from the tested pipe section by the central plate, has an inner space to be filled with liquid to exert a compensating axial force on the tested pipe section. The two horizontal oil pressure cylinders are respectively mounted next to upper and lower sides of the tested pipe section, exerting a horizontal force on the central plate. The vertical oil pressure cylinder is mounted below the central plate, exerting a vertical force on the central plate. The connecting tube connects the tested pipe section and the compensating pipe section for compensating any pressure difference.

2 Claims, 2 Drawing Sheets

CONTINUOUS TESTING DEVICE FOR WATER PIPE

BACKGROUND OF THE INVENTION

1. Field of the Invention

The present invention relates to a continuous testing device for a water pipe, particularly to a continuous testing device for detecting volume changes due to axial pressure.

2. Description of Related Art

For manufacturing of flexible pipes, appropriate material for practical use needs to be employed. Testing of material samples is performed to ensure that requirements are met.

Flexible pipes are produced in various sizes, having inner diameters of up to 4000 mm. With water pressure in practice reaching 20 kg/cm$^2$, axial forces on water pipes are as large as thousands of tons, and large mechanisms (usually oil pressure cylinders) are required to overcome axial pressure. Testing of flexible pipes for expansion, deflection and eccentricity under pressure is fraught with difficulties, since high water pressure readily leads to changes of length and volume. Due to the incompressibility of liquid, a small volume change immediately leads to a large pressure change, and a stable condition cannot be achieved. Therefore, if there is no way to release or refill water, testing data of flexible pipes will turn out to be faulty, and the testing process will have to be stopped.

A conventional testing device for a flexible pipe used in manufacturing plants, as shown in FIG. 2, comprises: a frame 100, carrying mechanical weight; a fixed plate 101; a movable plate 102, two joints 106; two horizontal oil pressure cylinders 104; and a vertical oil pressure cylinder 105. The fixed plate 101 is mounted on one end of the frame 100, providing a fixed base for testing shifts of a flexible pipe section 107, and has two canals leading to the flexible pipe section 107 to which an inlet 101a and an outlet 101b are respectively connected for applying pressure. The two horizontal joints 106 are connected with an upper end and a lower end of the fixed plate 101, respectively, having far ends connected with the movable plate 102, with threaded bolts 103 passing through the movable plate 102 serving to adjust holding forces. The two horizontal oil pressure cylinders 104 are connected with the upper and lower ends of the fixed end plate 101, respectively, exerting horizontal force on the movable plate 102. The vertical oil pressure cylinder 105 is set on a movable base 108 on the frame 100, applying vertical force on the movable plate 102.

During testing, the flexible pipe section 107 needs to withstand a large axial force. For the joints 106 and threaded bolts 103 carrying the axial load, water is let out of the flexible pipe and nuts 103a on the adjusting threaded bolts 103 are turned by a preset degree. Then water is through the inlet 101a filled into the flexible pipe. During filling, changes of length and shifting of the flexible pipe section 107 are sensed. However, since the nuts 103a on the threaded bolts 103 determine a fixed state, there is no way continually to monitor shifting of the tested pipe section 107. Thus several measurements require repeated adjusting of the nuts 103a on the threaded bolts 103, which is not a realistic test of the tested pipe section 107. In real use, the tested pipe section 107 undergoes continuous change of pressure. Therefore, conventional testing does not reveal real properties of the tested pipe section 107.

Above explanation shows that a conventional testing device for a water pipe has the following shortcomings:

1. Only discontinuous, static monitoring is possible, no continuous changes of pressure are simulated.
2. Testing in several steps is time-consuming and cumbersome.
3. Test data do not correspond to the behavior of the tested pipe and are imprecise, not providing a solid base for judging the properties of tested pipes.
4. Tests have a high rate of failure, wasting cost and effort.

SUMMARY OF THE INVENTION

It is the main object of the present invention to provide a continuous testing device for a water pipe allowing safe testing at low cost.

Another object of the present invention is to provide a continuous testing device for a water pipe for precise testing with reliable data.

The present invention can be more fully understood by reference to the following description and accompanying drawings.

DETAILED DESCRIPTION OF THE PREFERRED EMBODIMENT

Figure 1:
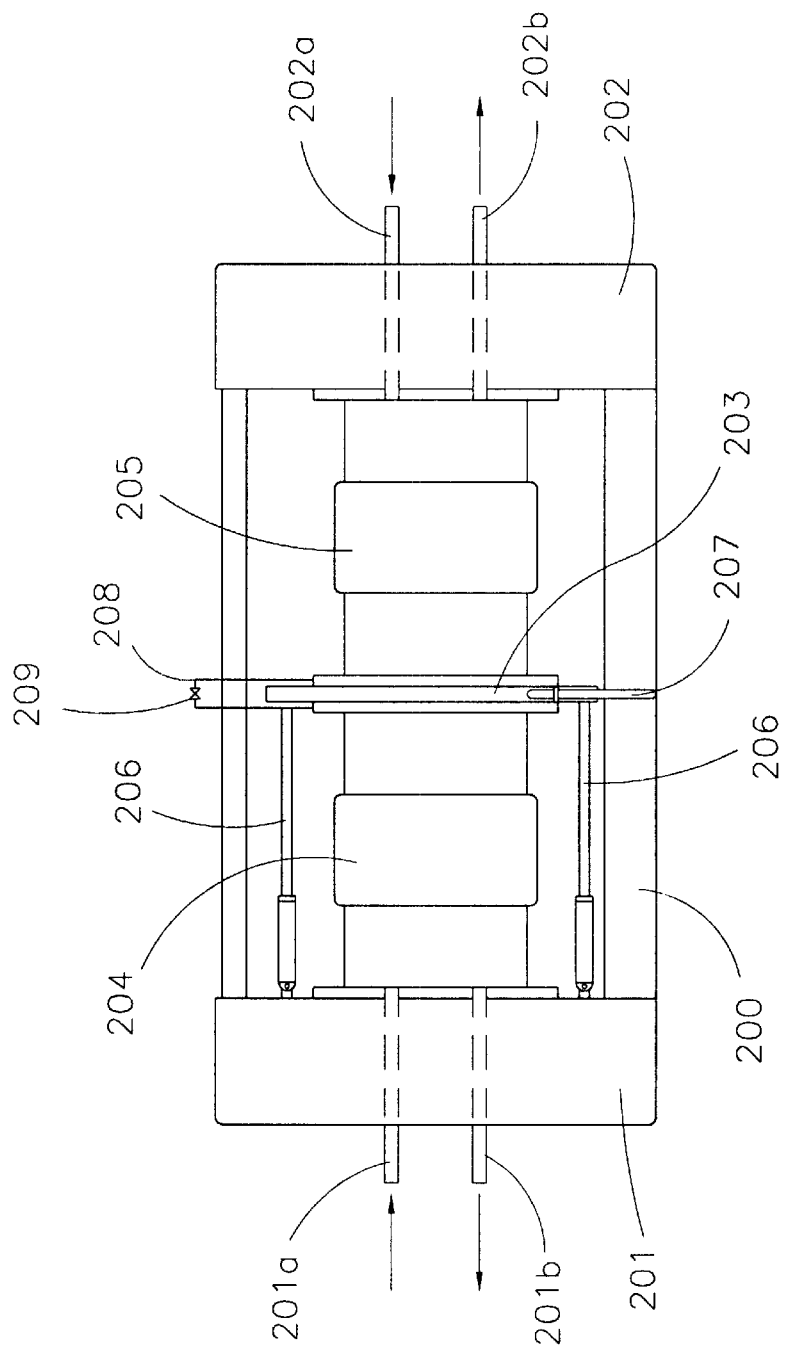
FIG. 1 is a schematic illustration of the continuous testing device for a water pipe of the present invention.
Figure 2:
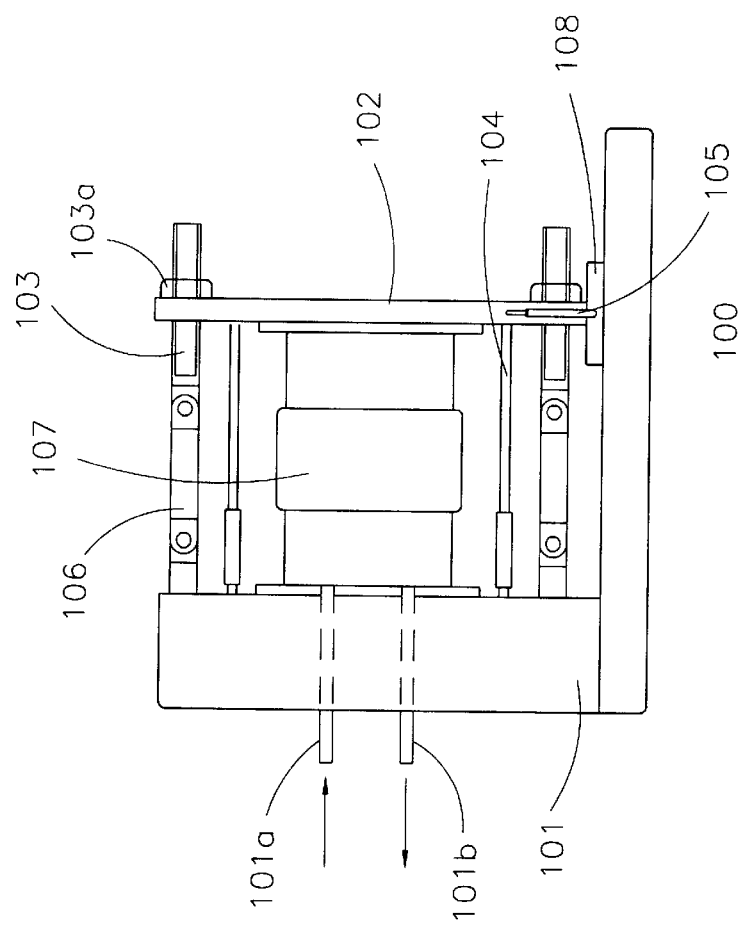
FIG. 2 is a schematic illustration of a conventional testing device for a water pipe.

As shown in FIG. 1, the continuous testing device for a water pipe of the present invention in a first embodiment mainly comprises: a frame 200, carrying mechanical weight; a left fixed plate 201 and a right fixed plate 202 at left and right ends of the frame; a tested pipe section 204, being a tube body that allows monitoring, located to the right of the left fixed plate 201, with the left and right fixed plates 201, 202 providing fixed bases for measuring shifting thereof; a compensating pipe section 205, located to the left of the right fixed plate at a position symmetrical to the position of the tested pipe section 204 and filled with liquid to exert a compensating axial force on the tested pipe section 204; a central plate 203, separating the tested pipe section 204 and the compensating pipe section 205, providing a base for shifting of the tested pipe section 204; two horizontal oil pressure cylinders 206; a vertical oil pressure cylinder 207; and a connecting tube 208. The left and right fixed plates 201, 202 each have two canals leading to the pipe sections 204, 205, respectively, to which inlets 201a, 202a and outlets 201b, 202b are respectively connected for applying pressure. The two horizontal oil pressure cylinders 206 are respectively connected with upper and lower ends of the left fixed plate 201 and with upper and lower ends of the central plate 203 exerting horizontal force on the central plate 203. The vertical oil pressure cylinder 207 has an upper end fastened to the lower end of the central plate 203 and a lower end set on frame 200, applying vertical force on the central plate 203. The connecting tube 208 straddles the upper end of the central plate 203, connecting the tested pipe section 204 and the compensating pipe section 205 for compensating any pressure difference.

The main characteristic of the present invention lies in employing the compensating pipe section 205, which is balanced against the tested pipe section 204. The compensating pipe section 205 and the tested pipe section 204 have equal inner diameters. When pressure inside the tested pipe section 204 rises due to liquid entering the inlet 201a, the compensating pipe section 205 experiences higher pressure due to liquid entering the inlet 202a. Pressure differences between the tested pipe section 204 and the compensating pipe section 205 are compensated by the connecting tube 208, resulting in equal pressures inside the tested pipe section 204 and the compensating pipe section 205.

The central plate 203 is inserted between the tested pipe section 204 and the compensating pipe section 205, being at the upper and lower ends thereof connected with the horizontal oil pressure cylinders 206 and at the lower end thereof being connected with the vertical oil pressure cylinder 207. When the central plate 203 is on both sides exposed to higher pressure due to increased pressure inside the tested pipe section 204 and the compensating pipe section 205, axial water pressure between the tested pipe section 204 and the compensating pipe section 205 is balanced. At this time, the central plate is shifted by undergoing forces from the horizontal and vertical oil pressure cylinders 206, 207, causing axial and transversal shifts of the tested pipe section 204 and allowing continuous monitoring, so that test data are obtained according to practice.

The connecting tube 208 on the upper end of the central plate, compensating pressure differences between the tested pipe section 204 and the compensating pipe section 205, has a blocking valve 209 for controlling flow of liquid through the connecting tube 208. When testing is started, the blocking valve 209 is opened, allowing free flow through the connecting tube 208 and compensating of pressure differences between the tested pipe section 204 and the compensating pipe section 205. Since a pressure increase in the tested pipe section 204 leads to a volume expansion, refilling of liquid is required. On the other hand, when the compensating pipe section 205 is exposed to axial pressure by the tested pipe section 204, compression thereof results, and liquid of the same quantity needs to be squeezed out. After opening the blocking valve 209, liquid from the compensating pipe section 205 refills the tested pipe section 204. Thus in any state of the tested pipe section 204 uniform and stable forces are maintained, and continuous expansion and contraction are simulated, allowing for smooth testing even of large pipes. Obtained data correspond to practical use of water pipes, so that appropriate testing is performed.

As above explanation shows, the continuous testing device for a water pipe of the present invention has the following advantages:

1. Testing under continuously varying pressure is possible, so that simulation data of practical use are obtained.
2. Usage is easy, and little time for testing is required.
3. Precise data are obtained, providing valuable information for manufacturing.
4. The test failure rate is low, minimizing cost and expenses.

While the invention has been described with reference to a preferred embodiment thereof, it is to be understood that modifications or variations may be easily made without departing from the spirit of this invention which is defined by the appended claims.

What is claimed is:

1. A continuous testing device for a water pipe, comprising a frame, carrying mechanical weight;

a left fixed plate and a right fixed plate at left and right ends of said frame, providing fixed bases;

a tested pipe section, being a tube body that allows monitoring, located between said left and right fixed plates next to said left fixed plate;

a compensating pipe section, located between said left and right fixed plates next to said right fixed plate and having an inner space to be filled with liquid to exert a compensating axial force on said tested pipe section;

a central plate, separating said tested pipe section and said compensating pipe section;

two horizontal oil pressure cylinders, respectively mounted next to upper and lower sides of said tested pipe section, having left ends fastened to said left fixed plate and right ends fastened to said central plate and exerting a horizontal force on said central plate;

a vertical oil pressure cylinder, mounted below said central plate, having an upper end fastened to a lower end of said central plate and a lower end set on said frame and exerting a vertical force on said central plate; and a connecting tube, connecting said tested pipe section and said compensating pipe section for compensating any pressure difference;

wherein due to compensation of pressures inside said tested pipe section and said compensating pipe section, axial forces are balanced and, by operating said horizontal and vertical oil pressure cylinders, axial expansion and contraction as well as transversal bending of said tested pipe section are monitored under defined pressure loads.

2. A continuous testing device for a water pipe according to claim 1, wherein said connecting tube has a blocking valve for controlling flow of liquid through said connecting tube.

* * * * *